(12) United States Patent
Furner

(10) Patent No.: US 9,204,625 B2
(45) Date of Patent: Dec. 8, 2015

(54) DISPENSER

(75) Inventor: Paul E. Furner, Waterford, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 478 days.

(21) Appl. No.: 13/588,974

(22) Filed: Aug. 17, 2012

(65) Prior Publication Data

US 2014/0048616 A1  Feb. 20, 2014

(51) Int. Cl.
*B05B 1/30* (2006.01)
*A01M 1/20* (2006.01)
*A61L 9/14* (2006.01)
*B65D 83/28* (2006.01)
*B65D 83/38* (2006.01)
*B05B 1/26* (2006.01)

(52) U.S. Cl.
CPC ............ *A01M 1/2038* (2013.01); *A01M 1/2044* (2013.01); *A61L 9/14* (2013.01); *B65D 83/285* (2013.01); *B65D 83/384* (2013.01); *A61L 2209/111* (2013.01); *B05B 1/262* (2013.01); *B05B 1/267* (2013.01)

(58) Field of Classification Search
USPC .................. 239/569, 579, 302, 337, 338, 339
See application file for complete search history.

(56) References Cited

U.S. PATENT DOCUMENTS

| | | | |
|---|---|---|---|
| 2,951,644 A | 9/1960 | Mahon et al. | |
| 3,330,481 A | 7/1967 | Dearling | |
| 3,972,473 A | 8/1976 | Harrison | |
| 4,084,732 A * | 4/1978 | Dearling | 222/402.17 |
| 4,141,472 A * | 2/1979 | Spitzer et al. | 222/189.01 |
| 4,200,229 A | 4/1980 | Spector | |
| 4,235,373 A | 11/1980 | Clark | |
| 4,341,348 A | 7/1982 | Dearling | |
| 4,346,059 A | 8/1982 | Spector | |
| 4,354,638 A * | 10/1982 | Weinstein | 239/337 |
| 4,356,969 A | 11/1982 | Obermayer et al. | |
| D274,040 S | 5/1984 | Ridgley | |
| D285,842 S | 9/1986 | Tigert | |
| D285,843 S | 9/1986 | Tigert | |
| D285,844 S | 9/1986 | Tigert | |
| 4,726,519 A | 2/1988 | Muoio | |
| 4,805,839 A * | 2/1989 | Malek | 239/337 |
| 4,889,284 A | 12/1989 | Spector | |
| D309,943 S | 8/1990 | Jones et al. | |
| D309,996 S | 8/1990 | Gearing | |
| D310,021 S | 8/1990 | Anderson | |
| D318,746 S | 7/1991 | Austin | |
| D326,816 S | 6/1992 | Abrams | |
| D355,712 S | 2/1995 | Barlics | |
| D366,803 S | 2/1996 | Hauser et al. | |
| D380,641 S | 7/1997 | Randle | |

(Continued)

FOREIGN PATENT DOCUMENTS

DE  2540075 A1  3/1977
EM  000025333-0001  5/2003

(Continued)

OTHER PUBLICATIONS

PCT/US2013/055300 International Search Report dated Nov. 25, 2013.

*Primary Examiner* — Justin Jonaitis

(57) ABSTRACT

A dispensing device includes a housing, a substrate having a surface and disposed within the housing, a reservoir disposed within the housing and having a volatile active, and an activator operatively connected to the reservoir. When the activator is activated, the volatile active is released from the reservoir onto the surface to create a first quantity of volatile active having a first emanation rate and a second quantity of volatile active having a second emanation rate.

7 Claims, 4 Drawing Sheets

(56) References Cited

U.S. PATENT DOCUMENTS

| | | |
|---|---|---|
| 5,704,259 A | 1/1998 | Riehle |
| 5,765,751 A | 6/1998 | Joshi |
| 5,802,933 A | 9/1998 | Hebert et al. |
| 5,810,253 A | 9/1998 | Ohayon |
| 5,849,264 A | 12/1998 | Bassam et al. |
| 5,899,382 A | 5/1999 | Hayes et al. |
| D414,060 S | 9/1999 | Talbot-Titley |
| 6,131,488 A | 10/2000 | Coonrad |
| D437,040 S | 1/2001 | Soller et al. |
| 6,202,511 B1 | 3/2001 | Murray et al. |
| 6,250,181 B1 | 6/2001 | Coonrad |
| 6,283,337 B1 | 9/2001 | Nakamura et al. |
| 6,338,424 B2 | 1/2002 | Nakamura et al. |
| 6,360,477 B1 | 3/2002 | Flashinski et al. |
| D456,663 S | 5/2002 | Chew |
| 6,534,079 B1 | 3/2003 | Munagavalasa |
| D474,109 S | 5/2003 | Owens |
| 6,569,387 B1 | 5/2003 | Furner et al. |
| 6,610,254 B1 | 8/2003 | Furner et al. |
| 6,723,671 B2 | 4/2004 | Zolotarsky et al. |
| D489,642 S | 5/2004 | Brumlow |
| D492,600 S | 7/2004 | Moore |
| D499,796 S | 12/2004 | Walker |
| D501,248 S | 1/2005 | Chi-Hsiang et al. |
| D502,365 S | 3/2005 | Dretzka |
| D508,594 S | 8/2005 | Snell |
| 6,923,432 B1 | 8/2005 | Martinez |
| 6,957,779 B2 | 10/2005 | Joshi et al. |
| D515,682 S | 2/2006 | LaBlaine |
| 7,066,052 B2 | 6/2006 | Chen |
| 7,134,363 B2 | 11/2006 | Krallman |
| 7,137,534 B2 | 11/2006 | Patel |
| 7,149,417 B2 | 12/2006 | Joshi et al. |
| D538,992 S | 3/2007 | Snell |
| 7,234,648 B2 | 6/2007 | Tepper et al. |
| D550,509 S | 9/2007 | Dretzka et al. |
| D557,073 S | 12/2007 | Snell |
| D561,929 S | 2/2008 | Meeker et al. |
| D565,239 S | 3/2008 | Meeker et al. |
| D565,783 S | 4/2008 | Meeker et al. |
| D573,917 S | 7/2008 | Bigoski |
| D575,899 S | 8/2008 | Meeker et al. |
| D576,759 S | 9/2008 | Meeker et al. |
| D582,724 S | 12/2008 | Dretzka |
| D588,852 S | 3/2009 | Stein |
| 7,549,598 B2 | 6/2009 | Tepper et al. |
| D596,074 S | 7/2009 | Bodum |
| D600,547 S | 9/2009 | Cain |
| 7,600,697 B2 | 10/2009 | Bankers et al. |
| D604,824 S | 11/2009 | Paolazzi et al. |
| D612,976 S | 3/2010 | Meeker et al. |
| D616,139 S | 5/2010 | Meeker et al. |
| D616,594 S | 5/2010 | Meeker et al. |
| D620,569 S | 7/2010 | Hall, Jr. et al. |
| D625,460 S | 10/2010 | Boissevain |
| 7,887,759 B2 | 2/2011 | Triplett |
| D634,415 S | 3/2011 | Abbondanzio et al. |
| D638,112 S | 5/2011 | Hisey et al. |
| D639,704 S | 6/2011 | Harshman |
| 8,047,099 B2 | 11/2011 | St. John et al. |
| D651,518 S | 1/2012 | Padain et al. |
| D652,500 S | 1/2012 | Abbondanzio et al. |
| D652,661 S | 1/2012 | Lipfert et al. |
| D659,886 S | 5/2012 | Wauters |
| D660,940 S | 5/2012 | Flowers et al. |
| D667,151 S | 9/2012 | Arslanian |
| 8,261,634 B2 | 9/2012 | St. John et al. |
| D672,858 S | 12/2012 | Abbondanzio et al. |
| D673,252 S | 12/2012 | Abbondanzio et al. |
| D680,858 S | 4/2013 | Clark et al. |
| D681,299 S | 4/2013 | Lai |
| 2004/0144864 A1* | 7/2004 | Valpey et al. .......... 239/337 |
| 2005/0275118 A1 | 12/2005 | Chen |
| 2006/0110297 A1 | 5/2006 | D'Amico et al. |
| 2007/0057084 A1 | 3/2007 | Vieira |
| 2007/0140924 A1 | 6/2007 | Hill |
| 2007/0187524 A1 | 8/2007 | Sherwood |
| 2008/0311008 A1 | 12/2008 | Tranzeat |
| 2009/0121041 A1 | 5/2009 | DeFlorian et al. |
| 2010/0038609 A1 | 2/2010 | Chen |
| 2010/0196195 A1 | 8/2010 | Moschel |
| 2010/0322892 A1 | 12/2010 | Burke |
| 2011/0120270 A1 | 5/2011 | Lombardi et al. |
| 2012/0091409 A1 | 4/2012 | Hanlon |
| 2012/0104027 A1 | 5/2012 | Hoppe et al. |
| 2012/0108888 A1 | 5/2012 | Spector |
| 2012/0111966 A1 | 5/2012 | Barlow et al. |
| 2012/0187217 A1 | 7/2012 | Maget et al. |

FOREIGN PATENT DOCUMENTS

| | | |
|---|---|---|
| EM | 000048137-0001 | 6/2003 |
| EM | 000126453-0002 | 1/2004 |
| EM | 0001476320001 | 1/2004 |
| EM | 0001468240003 | 6/2004 |
| EM | 0002328060001 | 9/2004 |
| EM | 0003640540001 | 6/2005 |
| EM | 0003640540003 | 6/2005 |
| EM | 0003640540004 | 6/2005 |
| EM | 0004071430001 | 9/2005 |
| EM | 0004575100003 | 1/2006 |
| EM | 000601562-00003 | 9/2006 |
| EM | 0008347260001 | 11/2007 |
| EM | 000889043-0001 | 2/2008 |
| EM | 001596388-0002 | 7/2009 |
| EM | 001660846-0006 | 1/2010 |
| EM | 001693458-0001 | 4/2010 |
| EM | 001928466-0006 | 10/2011 |
| EM | 002051540-0003 | 6/2012 |
| EM | 002079103-0001 | 7/2012 |
| FR | 2594714 A1 | 8/1987 |
| FR | 013047-019 | 9/2001 |
| FR | 013047-023 | 9/2001 |
| FR | 013047-024 | 9/2001 |
| FR | 015603-005 | 12/2001 |
| FR | 096251-002 | 6/2010 |
| GB | 1148408 A | 4/1969 |
| GB | 3001196 | 3/2002 |
| HU | R01936899 | 10/2011 |
| JP | S53139606 U | 11/1978 |
| JP | H01165039 U | 11/1989 |
| JP | 2001088877 A | 4/2001 |
| JP | 2004033609 A | 2/2004 |
| JP | 2004034009 A | 2/2004 |
| JP | 2014-058455 A | 4/2014 |
| PL | 806 | 11/2003 |
| PL | 6239 | 6/2005 |
| PL | 11394 | 11/2007 |
| PL | 14495 | 1/2010 |
| WO | 85/00290 A1 | 1/1985 |
| WO | DM047591 | 3/1999 |
| WO | DM/048626 | 7/1999 |
| WO | DM/052724 | 7/2000 |
| WO | DM/062973 | 11/2000 |
| WO | DM/058560 | 8/2001 |
| WO | DM/061226 | 7/2002 |
| WO | 2004096588 | 11/2004 |
| WO | 2005044320 | 5/2005 |
| WO | 2006002395 | 1/2006 |
| WO | 2006105347 | 10/2006 |
| WO | 2006134353 | 12/2006 |
| WO | 2007062471 | 6/2007 |
| WO | 2008124957 | 10/2008 |
| WO | DM/073042 | 9/2009 |
| WO | DM/074638 | 9/2010 |
| WO | 2002083043 | 10/2010 |
| WO | DM/075051 | 10/2010 |
| WO | DM/078953 | 11/2011 |
| WO | DM/077883 | 12/2011 |
| WO | DM/078938 | 2/2012 |
| WO | 2012059771 | 5/2012 |

* cited by examiner

DISPENSER

CROSS REFERENCE TO RELATED APPLICATIONS

Not applicable.

REFERENCE REGARDING FEDERALLY SPONSORED RESEARCH OR DEVELOPMENT

Not applicable.

SEQUENTIAL LISTING

Not applicable.

BACKGROUND OF THE INVENTION

1. Field of the Invention

The present invention relates generally to a dispenser for dispensing a fluid or product from a spray device, and more particularly, to an apparatus for discharging a product from a dispensing system to create portions of the product with different emanation rates.

2. Description of the Background of the Invention

Insecticide and/or fragrance dispensing devices are typically either active, where a composition is released from a reservoir upon activation of a release mechanism, or passive, where the composition emanates from a pre-charged substrate by passive diffusion. Each system has it advantages over the other. For example, active systems enable a user to quickly release a desired amount of an insecticide or a fragrance into the environment to repel insects or overcome a strong odor. However, these spikes in composition intensity usually decay rapidly. On the other hand, while passive systems do not have the ability to release desired amounts of a composition upon activation, they typically have a more subtle decay in the intensity of the composition compared to active systems.

Others have sought to combine active and passive systems to take advantage of the controlled release of the active systems and the sustained release of the passive systems. For example, one dispensing device dispenses a spray directly into the air and into an absorbent member. The dispensing device includes an aerosol container and an overcap disposed on a top of the aerosol container. The overcap includes a vented cylindrical sidewall and a vented top portion. A plunger element engages a valve stem on the container and extends through the top portion of the overcap. The plunger includes two ports formed on opposing sides thereof. Two absorbent carrier members are disposed within an upper portion of the overcap around the plunger element. The carrier members are substantially semicircular in cross-section and are spaced around the plunger in such a way as to create two diametrically opposing passageways. Upon activation of the plunger element, fragrance is released out of the ports and through the opposing passageways into the atmosphere. The overcap may also be turned 90 degrees so that the ports and passageways do not align, such that when the plunger is activated spray is released out of the ports directly into the carrier elements. Additional ports may be provided in the plunger so that the spray can be released through the passageways and onto the carrier members simultaneously.

Another device simultaneously sprays an air-treating composition into the air for instant air treatment and recharging an absorbent element for effective continuous air treatment. The device includes an overcap for an aerosol container that includes a cylindrical vented wall and an actuator button with a passageway in communication with a valve stem of the aerosol container. The absorbent member is disposed within the overcap. When the device is activated, the air-treating composition passes a plurality of outlets formed in the passageway before being discharged through a spray orifice and into the air. The plurality of outlets direct a portion of the air-treating composition onto the absorbent member for subsequent passive treatment of the air. A preferred embodiment includes four outlets spaced at 90 degree intervals around the passageway. Alternatively, the outlets could be formed in the valve stem of the aerosol container instead of in the passageway.

Similarly, an additional vapor dispensing device includes multiple delivery mechanisms for fragrance release. The dispensing device includes a continuous delivery mechanism with an emanator in communication with a reservoir, for delivering a first continuous passive release of fragrance. The dispensing device also includes an on-demand delivery mechanism for delivering an instantaneous burst of fragrance. Additionally, activation of the on-demand delivery mechanism produces a second continuous passive release of fragrance by depositing a portion of the fragrance burst onto the continuous delivery mechanism or a second surface. The combination of the first and second passive releases creates a release of fragrance that is of a higher intensity than the fragrance released by the continuous delivery mechanism alone.

However, none of these dual systems recognizes the advantages of the current system that uses the relationship between the active delivery of a composition and the passive emanator surface to create an insecticide (or other volatile active) dispensing system with multiple emanation rates for a single composition.

SUMMARY OF THE INVENTION

According to one aspect, a dispensing device includes a housing, a substrate having a surface and disposed within the housing, a reservoir disposed within the housing and comprising a volatile active, and an activator operatively connected to the reservoir. When the activator is activated, the volatile active is released from the reservoir onto the surface to create a first quantity of volatile active having a first emanation rate and a second quantity of volatile active having a second emanation rate.

According to another aspect, a dispensing device includes a housing, a substrate, a reservoir including a composition having a volatile active and a liquid carrier, and an activator operatively connected to the reservoir. When the activator is activated, a stream of the composition is released from the reservoir to impact a surface of the substrate. Upon impact of the composition a first portion X of the composition is deflected out of the dispensing device and a second portion Y of the composition is deposited onto the surface of the substrate. The ratio X/Y is variable.

According to a further aspect, a dispensing device includes a housing comprising a surface, a reservoir comprising a composition, and an activator operatively connected to the reservoir. When the activator is activated, the composition is released from the reservoir onto the surface to create a first quantity of the composition having a first emanation rate, a second quantity of the composition having a second emanation rate, and a third quantity of the composition having a third emanation rate.

DETAILED DESCRIPTION

Figure 1:
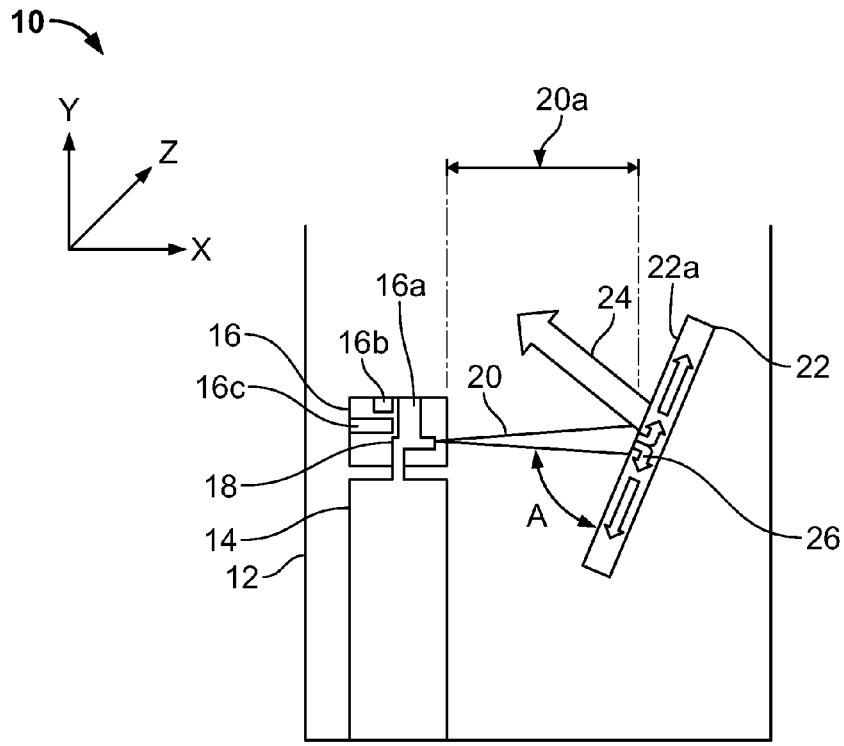
FIG. 1 is a schematic elevational view of one embodiment of a dispenser.
Figure 1A:
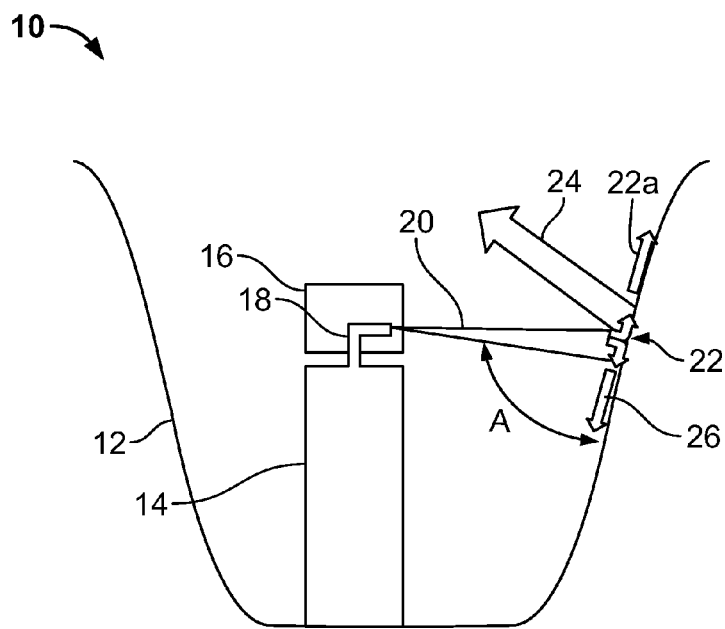
FIG. 1A is a schematic elevational view of another embodiment of a dispenser with a substrate integral with the dispenser housing.
Figure 2:
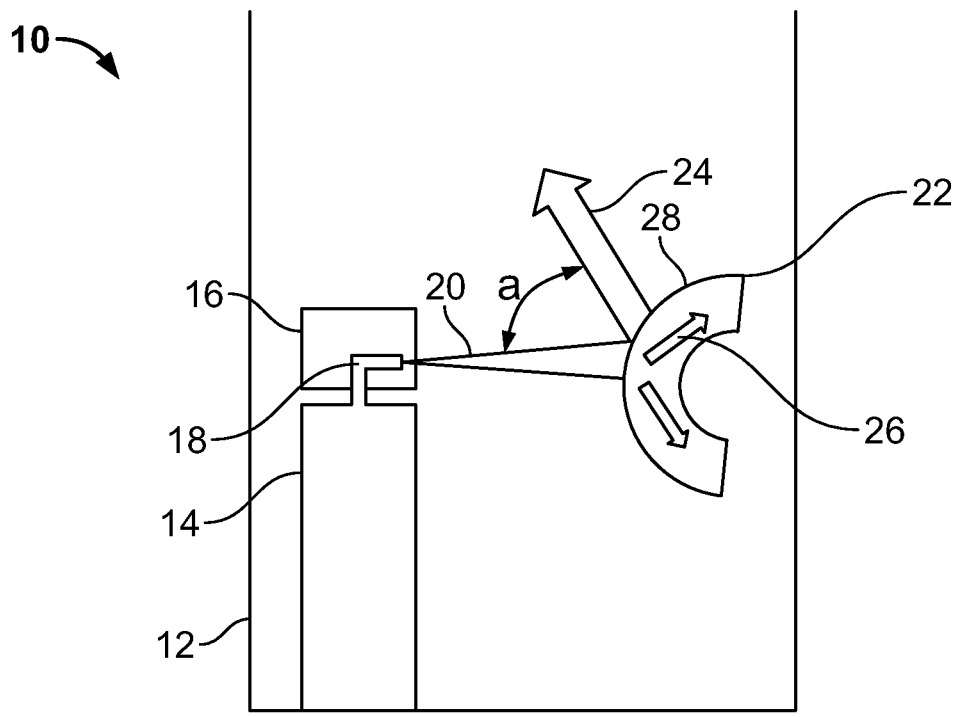
FIG. 2 is a schematic elevational view of another embodiment of a dispenser with a shaped substrate.
Figure 3:
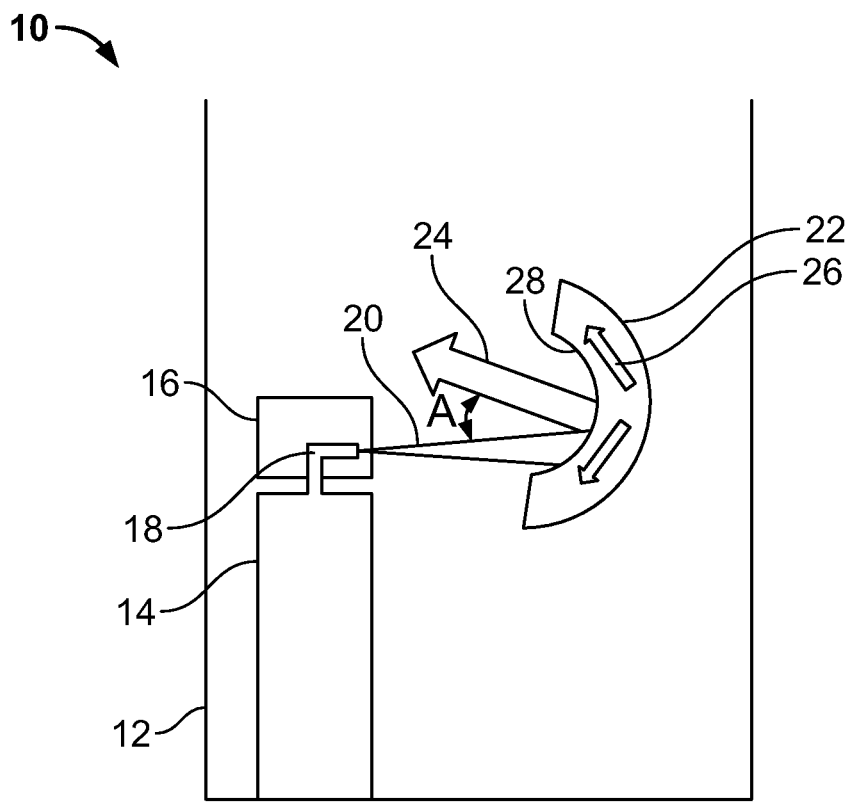
FIG. 3 is a schematic devotional view of a further embodiment of a dispenser with a shaped substrate.
Figure 4:
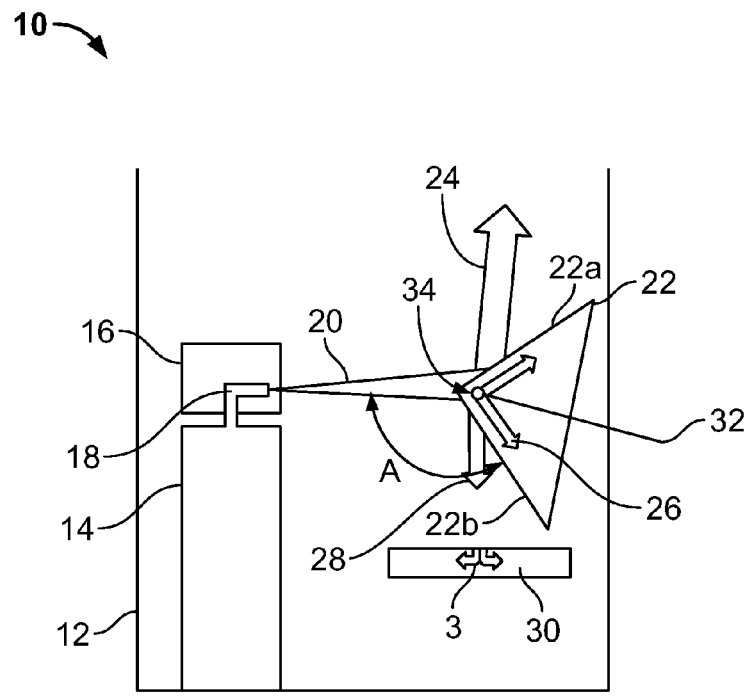
FIG. 4 is a schematic elevational view of another embodiment of a dispenser with a control mechanism to change an amount of a composition deflected from and deposited on a substrate.
Figure 5:
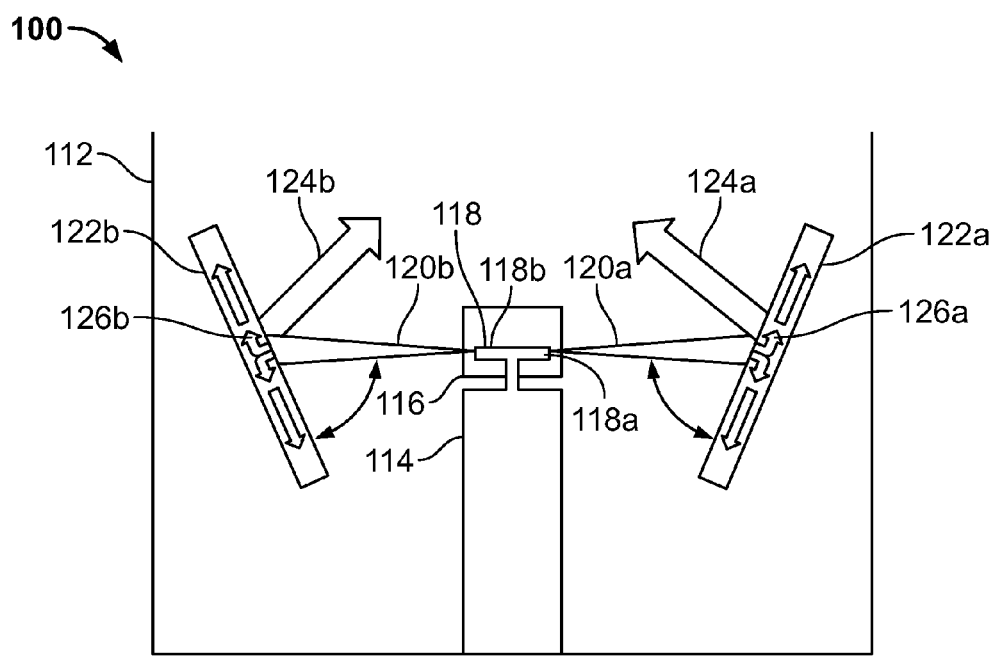
FIG. 5 is a schematic elevational view of another embodiment of a dispenser with a plurality of nozzles and substrates.
Figure 6:
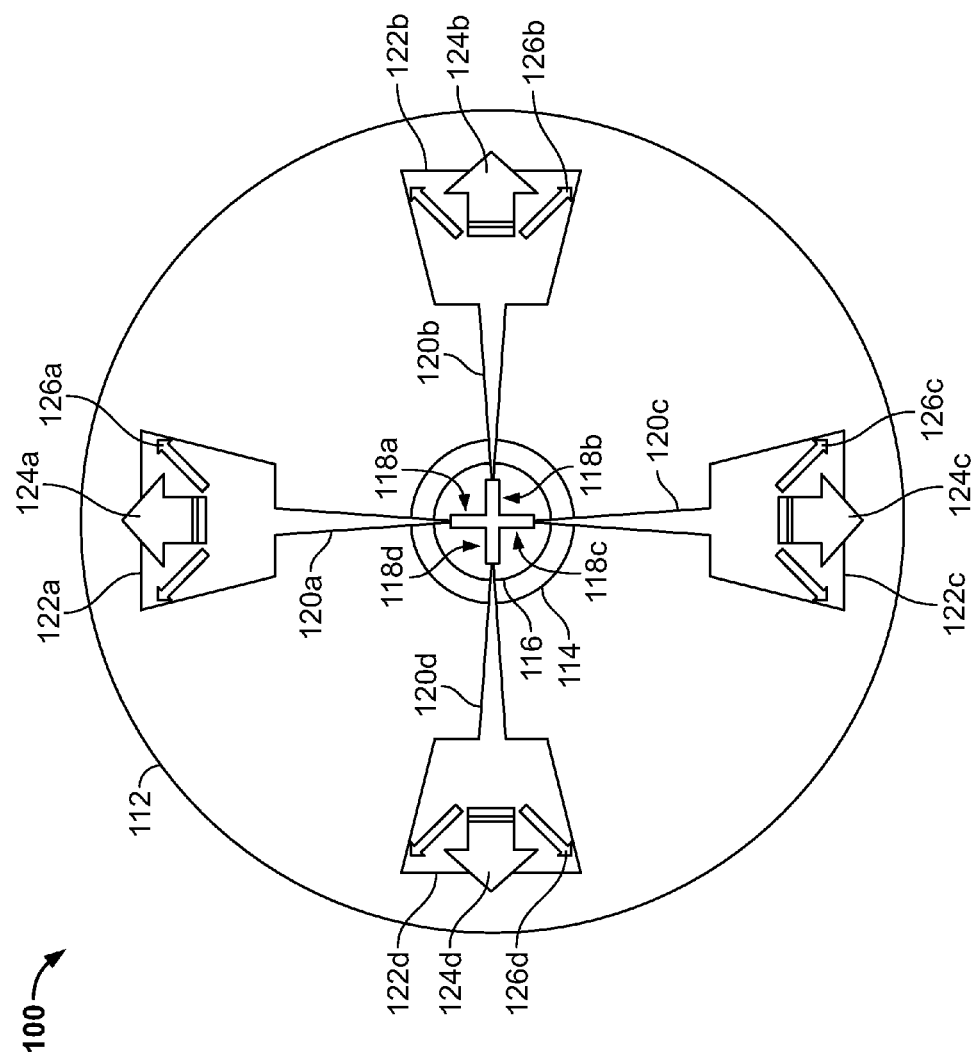
FIG. 6 is a schematic top plan view of a variation of the embodiment of the dispenser shown in FIG. 5.

The present disclosure is directed toward dispensers for dispensing volatile active-containing compositions. The dispensers described herein may be used either as stand alone dispenser devices, which may be placed on a table, shelf or other flat surface, or as personal devices that may be carried on a person or animal. FIG. 1 illustrates a first embodiment of a dispenser 10 that includes a housing 12, a reservoir 14 that contains a composition to be dispensed, and an activator 16 that releases the composition from the reservoir by way of a nozzle 18. The housing 12 may be constructed from any suitable material, such as a plastic, a PET non-woven substrate, a metal, glass, or combinations thereof. Additionally, the materials may include combinations of manufactured, natural, and recycled or reclaimed materials. In some cases, the materials are selected from, or include manufactured materials configured to approximate, naturally occurring substances, such as wood, stone, paper, or rock, or combinations thereof. Any such materials can be selected based upon their having a natural looking appearance and/or a natural feeling to the touch. By incorporating natural materials, or analogs of natural materials, the dispenser 10 can be made to look more appropriate for placement in an outdoors location, such as in a sun room or on a balcony, or can complement the look and feel of existing natural objects within the home.

The dispenser 10 is configured to discharge a composition from one or more reservoirs 14 disposed within the housing 12 upon the occurrence of a particular condition. The condition could be the manual activation of the dispenser 10 by way of the activator 16, which may include a manual push button 16a that opens a valve of the reservoir that may be depressed by a user. In another embodiment, the activator 16 may include additional and/or alternate mechanisms to release the composition from the reservoir. For example, the activator 16 may include a solenoid 16b operatively connected to the reservoir Valve.

The condition could also be an automatic activation of the activator by, for example, a mechanical or electromechanical system that activates the device in response to an elapsed time interval or signal from a sensor, such as a motion sensor or other type of sensor. In one implementation, a sensor 16c may be a light-sensing element, such as a photodetector or photodiode light detector, photoresistor, photodiode, phototransistor, or a passive infra-red sensor. For example, automatic activation of the activator may activate a solenoid powered by batteries held within the housing that depresses a valve in the reservoir to release the composition therein.

The reservoir may be an aerosol container and the like. Additional examples of reservoirs, activation mechanisms, compositions, substrates, and the like that may be used herein include those disclosed in U.S. Pat. Nos. 7,837,065, 8,061, 562, and U.S. patent application Ser. Nos. 11/801,554, 11/893,456, 11/893,489, 11/893,476, 11/805,976, and 11/893,532.

In another embodiment, the reservoir may include a chamber for holding the volatile active-containing composition, a Venturi throat or chamber in fluid communication with the composition within the chamber, and an air compressor. In this embodiment, activation of the reservoir 14 by the activator 16 causes compressed air to be forced through the Venturi chamber, thereby releasing an aerosolized volatile active-containing composition.

Upon activation of the activator 16, a stream 20 of the composition held within the reservoir 14 is released onto a substrate 22. The stream 20 may have spray patterns that are typically in the form of dispersions, and the spray emitted from a nozzle will form a dispersed spray pattern angle when viewed from the side (as depicted in FIGS. 1-6). The stream 20 of spray referred to herein is generally the central axis that bisects such a spray pattern. It is understood that portions of the stream will typically be distributed on either side of this central axis. The composition dispensed may include a fragrance, insecticide, a deodorizer, a fungicide, a bacteriocide, a sanitizer, a pet barrier, or other active volatile or other compound disposed within a earner liquid (for example an oil-based and/or water-based carrier), a deodorizing liquid, or the like. For example, the fluid may comprise OUST™, an air and carpet sanitizer for household, commercial, and institutional use, or GLADE®, a household deodorant, both sold by S. C. Johnson and Son, Inc., of Racine, Wis. The fluid may also comprise other actives, such as sanitizers, air and/or fabric fresheners, cleaners, odor eliminators, mold or mildew inhibitors, insect repellents, and the like, or others that have aromatherapeutic properties. The fluid alternatively comprises any fluid known to those skilled in the art that can be dispensed from a container, such as those suitable for dispersal in the form of particles or droplets suspended within a gas and/or propelled by means of a propellant. The dispenser 10 is therefore adapted to dispense any number of different fluid or product formulations.

The substrate 22 may be made of any suitable material including a plastic, a polymer, a metal, a fabric, a nonwoven, a cellulosic material, glass, and combinations thereof. In one embodiment, the substrate 22 is a polyethylene terephthalate non-woven substrate. In another embodiment, the substrate 22 is an aluminum substrate. In a further embodiment, the substrate 22 is a multi layered substrate, for example, with a nonabsorptive bottom layer and an absorbent top layer. Any number of layers with varying degrees of absorptiveness and/or permeability are contemplated.

Further, the substrate 22 may have various textures and/or surface patterns, such as a rough surface, a smooth surface, a channeled surface, and combinations thereof. Thus, once the stream 20 impacts the surface 22a of the substrate 22, a first portion 24 of the stream may be deflected off of the substrate to create a plume and a second portion 26 may be partially absorbed into the substrate and/or distributed over the surface of the substrate by means of the surface features and/or properties of the substrate. Deflection in this context means the rebound of the composition off of the substrate, which may be affected by one or more of the velocity of the stream 20 at impact with the substrate 22, the angle A of the stream relative to the substrate surface 22a, the composition of the substrate, the texture of the substrate, the variations in the rheological characteristics of the composition, and the like. Therefore, upon activation of the dispenser 10, a volatile active contained within the composition is simultaneously charged onto a substrate 22 and deflected off of the substrate to form a plume of the volatile active. The plume may thus provide a burst of volatile active into the environment that quickly permeates the environment where the dispenser 10 is located. The second portion 26 that is deposited on and/or in the substrate 22 provides a source for passive emanation of the volatile active, which has a slower, more prolonged release of the volatile active, which may be attributed, in part, to the more protected environment within the dispenser 10. It is further envisioned that a portion of the plume may settle on surfaces surrounding the dispenser 10 to thereby create a secondary passive system that has an emanation rate potentially higher than that of the deposited composition within the dispenser due to the greater relative amount of air flow outside of the dispenser housing, but less than that of the plume.

The quantity of the composition deflected out of the dispenser 10 (for example, the first portion 24) relative to the quantity of the composition deposited within and/or on the dispenser (for example, the second portion 26) may be expressed in terms of a ratio X/Y, wherein X is the quantity of the deflected portion and Y is the quantity of the deposited portion. For example, when the first portion 24 and the second portion 26 are equal, then the ratio X/Y has a value of one, as equal portions of the composition have been deflected and deposited. It follows that when the first portion 24 is greater than the second portion 26, then the ratio has a value greater than one, and the inverse is true when the second portion 26 is greater that the first portion 24. Relative values of X/Y contemplated expressed in percentages include about 100/0, or about 90/10, or about 80/20, or about 70/30, or about 60/40, or about 50/50, or about 40/60, or about 30/70, or about 20/80, or about 10/90, or about 0/100 and all values in between.

The substrate material and surface properties of the substrate 22 may affect the ratio X/Y of the first 24 and second portions 26. For example, a hard, hydrophobic, impermeable surface may be more likely to repel a water-based composition compared to a soft, hydrophilic, permeable surface. Thus, by changing not only the qualities of the composition, but by also changing the nature of the substrate 22, the ratio X/Y may be controlled. It is further envisioned that the surface properties of the substrate 22 may be hydrophobic, hydrophilic, soft, hard, liquid permeable, liquid impermeable and combinations thereof over portions thereof. For example, the surface 22*a* may have a checkered configuration with alternating hydrophobic and hydrophilic regions and/or hard and soft regions and/or liquid permeable and impermeable regions.

The ratio X/Y of the first 24 and second 26 portions of the composition may further be altered, for example, by varying an angle A (the angle measured between the central axis of the stream 20 and the substrate surface 22*a* as the substrate 22 pivots about the z-axis at the point of contact of the stream to the substrate) between the stream 20 and the surface 22*a* of the substrate 22 (see FIG. 1). For example, by decreasing the size of the angle A (when the lower portion of the substrate 22 pivots upward toward the stream 20), a greater area of impact of the stream on the surface 22*a* may be achieved. The larger area of impact leads to greater retention of the composition on the surface 22*a* and/or within the substrate 22, which leaves a smaller quantity to be deflected off.

In another embodiment, the ratio X/Y may be altered by varying the distance 20*a* traveled by the stream 20 between the nozzle 18 and the surface 22*a* for a given velocity of the stream. For example, the reservoir 14 may be placed closer or farther away from the substrate 22, which will increase the ratio X/Y and decrease the ratio X/Y, respectively.

Further, increasing or decreasing the caliber of the nozzle 18 (or orifice size) while maintaining a constant pressure within the reservoir 14, may cause the velocity of the stream 20 to decrease or increase, respectively. Moreover, the ratio X/Y may be determined, at least in part, by the nature of the stream 20, for example, whether it is a narrow jet or a V-shaped cone of a pressurized aerosol spray.

In another embodiment shown in FIG. 1A, the substrate 22 is integral with the housing 12. In this embodiment, the angle A between the stream 20 and the surface 22*a* of the substrate may be determined by the shape of the housing. For example, if the housing has a flared configuration as shown in FIG. 1A, which may resemble a flower or vase, and the like, the greater the flare of the housing, the smaller the angle A.

In a further embodiment shown in FIGS. 2 and 3, the shape of the surface 22*a* of the substrate 22 may influence the ratio X/Y. In FIG. 2, a convex-shaped substrate 22 may provide a larger area of impact for the stream on the substrate and therefore decrease the ratio if the substrate is absorptive of the composition. On the other hand, the convex shape may serve to further deflect the stream 20 in multiple directions, which would lead to an increased ratio X/Y. In FIG. 3, a concave surface 22*a* of the substrate 22 may serve to more efficiently deflect the stream 20 to increase the volume of the first portion 24 and the ratio X/Y.

In one embodiment shown in FIG. 4, the substrate 22 is both impermeable and designed to retain a minimal amount of the composition on its two surfaces 22*a* and 22*b* to be impacted by the stream 20 upon activation of the dispenser 10. In this embodiment, the portion of the stream 20 that impacts surface 22*a* is deflected to form the first portion 24 and the portion of the stream that impacts surface 22*b* is deflected to form a third portion 28. The second portion 26 is minimally deposited on both surfaces 22*a* and 22*b*. The first portion 24 may be deflected upwardly into the environment, whereas the third portion 28 may be deflected downward to be deposited onto a second substrate 30 that may provide an increased capacity for the dispenser 10 to serve as a passive emanator. Further envisioned in this embodiment is a control mechanism 32 that allows a user to change the ratio X/Y of the dispenser 10 by pivoting the substrate 22 about pivot 34. For example, by rotating the substrate 22 such that angle A is at an acceptable minimum, surface 22*b* is maximally exposed to the stream 20 and will deflect essentially all of the stream toward the secondary substrate 30. In this state, the dispenser 10 may be rendered completely passive, as the quantity of the first portion 24 is at or near zero. Conversely, by maximizing angle A, the dispenser may maximize the first portion 24 and thereby maximize the emanation rate of the volatile active into the surrounding environment.

In another embodiment similar to that in FIG. 4, the controller may be used to alter the shape of a flexible substrate to vary the ratio X/Y.

In another embodiment shown in FIGS. 5 and 6, a dispenser 100 has increased capacity for dispensing volatile active compositions. In FIG. 5, the housing 112 is configured to contain two substrates 122*a* and 122*b*, a reservoir 114, and an activator 116 that includes a dual direction nozzle 118 with two apertures 118*a* and 118*b* that fire two streams 120*a* and 120*b* onto the two substrates 122*a* and 122*b*, respectively. Here, the two streams 120*a* and 120*b* are deflected to form a first portion 124*a* and 124*b* in two parts, and a second portion in two parts 126*a* and 126*b* deposited onto the two substrates 122*a* and 122*b*. In this embodiment, it is envisioned that the ratio X/Y would be the same or similar to that of the embodiment shown in FIG. 1 assuming all variables to be the same.

In another embodiment shown in FIG. 6, the dispenser 100 includes a housing 112 configured to contain four substrates 122a-d, at least one reservoir 114, and an activator 116 that has four nozzles 118a-d. The four nozzles 118a-d fire four streams 120a-d onto the four substrates 122a-d to create a first portion in four parts 124a-d and a second portion in four parts 126a-d, respectively. Here, too, it is envisioned that the ratio X/Y would be the same or similar to that of the embodiment shown in FIG. 1 assuming all variables to be constant.

Additional features contemplated herein include use-up indicators. For example, in one embodiment where the volatile active is dispensed onto a substrate integral with the housing, an ink is provided within the walls of the housing or within the composition, which may appear or disappear to indicate when the volatile active has completely evaporated from the walls of the housing.

All documents cited in the Detailed Description of the Invention are, in relevant part, incorporated herein by reference, the citation of any document is not to be construed as an admission that it is prior art with respect to the present invention.

INDUSTRIAL APPLICABILITY

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

What is claimed is:

1. A dispensing device, comprising:
   a housing;
   a substrate;
   a reservoir disposed entirely within the housing, the reservoir holding a composition comprising a volatile active and a liquid carrier; and
   an activator operatively connected to the reservoir,
   wherein when the activator is activated, a stream of the composition is released from the reservoir to impact a surface of the substrate, and
   wherein upon impact of the composition a first portion X of the composition is deflected out of the dispensing device and a second portion Y of the composition is deposited onto the surface of the substrate, and
   wherein the ratio X/Y is variable.

2. The dispensing device of claim 1 further comprising a controller that allows a user to vary the ratio X/Y.

3. The dispensing device of claim 2, wherein the controller controls a contact angle between the stream and the surface of the housing wall.

4. The dispensing device of claim 3, wherein the substrate is impermeable to the volatile active.

5. The dispensing device of claim 1, wherein the reservoir comprises an aerosol container and a valve.

6. A dispensing device, comprising:
   a housing;
   a substrate including a pivot;
   a reservoir entirely disposed within the housing, the reservoir holding a composition comprising a volatile active and a liquid carrier; and
   an activator operatively connected to the reservoir,
   wherein when the activator is activated, a stream of composition is released from the reservoir to impact a surface of the substrate, and
   wherein upon impact of the composition a first portion X of the composition is deflected out of the dispensing device and a second portion Y of the composition is deposited onto the surface of the substrate, and
   wherein the ratio X/Y is variable by pivoting the substrate.

7. The dispensing device of claim 6, wherein the reservoir comprises an aerosol container and a valve.

* * * * *